(12) United States Patent
Zordan et al.

(10) Patent No.: US 9,176,055 B2
(45) Date of Patent: Nov. 3, 2015

(54) SYSTEM AND METHOD FOR MEASURING NARROW AND WIDE ANGLE LIGHT SCATTER ON A HIGH-SPEED CELL SORTING DEVICE

(71) Applicants: Michael D. Zordan, Champaign, IL (US); Gary P. Durack, Urbana, IL (US); Shinji Yamada, Kanagawa-ken (JP); Bharath K. Narahari, Spring Lake, MN (US); Elizabeth C. Eaton, Urbana, IL (US); Jeffrey D. Wallace, Mahomel, IL (US); Larry W. Arnold, Snow Camp, NC (US); Kevin A. Keilbach, Boulder, CO (US)

(72) Inventors: Michael D. Zordan, Champaign, IL (US); Gary P. Durack, Urbana, IL (US); Shinji Yamada, Kanagawa-ken (JP); Bharath K. Narahari, Spring Lake, MN (US); Elizabeth C. Eaton, Urbana, IL (US); Jeffrey D. Wallace, Mahomel, IL (US); Larry W. Arnold, Snow Camp, NC (US); Kevin A. Keilbach, Boulder, CO (US)

(73) Assignees: Sony Corporation, Tokyo (JP); Sony Corporation of America, New York, NY (US)

( * ) Notice: Subject to any disclaimer, the term of this patent is extended or adjusted under 35 U.S.C. 154(b) by 121 days.

(21) Appl. No.: 13/623,305

(22) Filed: Sep. 20, 2012

(65) Prior Publication Data

US 2013/0169953 A1 Jul. 4, 2013

Related U.S. Application Data

(60) Provisional application No. 61/583,074, filed on Jan. 4, 2012.

(51) Int. Cl.
*G01N 21/53* (2006.01)
*G01N 21/64* (2006.01)
(Continued)

(52) U.S. Cl.
CPC ............ *G01N 21/53* (2013.01); *G01N 15/1434* (2013.01); *G01N 15/1459* (2013.01);
(Continued)

(58) Field of Classification Search
CPC . G01N 15/147; G01N 15/14; G01N 15/1404; G01N 2015/149; G01N 2015/1493; G01N 2015/1486; G01N 21/64; G01N 2021/4726
USPC .............. 356/335–343, 72–73, 318; 359/359, 359/350, 361, 722, 588
See application file for complete search history.

(56) References Cited

U.S. PATENT DOCUMENTS 4,999,513 A * 3/1991 Ito et al. ......................... 250/575
5,173,808 A * 12/1992 Auer et al. ..................... 359/722
(Continued)

FOREIGN PATENT DOCUMENTS

| EP | 0442025 A1 | 6/1990 |
|----|------------|--------|
| EP | 0564122 A1 | 10/1993 |
| WO | WO 2005/033654 A2 | 4/2005 |

OTHER PUBLICATIONS

Luminex Life Science Assays, www.diax.it/applications/dettagli/Luminex Life Science Assays.html, Apr. 27, 2012, 3 pages.
(Continued)

*Primary Examiner* — Hoa Pham
(74) *Attorney, Agent, or Firm* — Ice Miller LLP

(57) ABSTRACT

The various embodiments disclosed herein utilize multiple lasers that have different wavelengths and a single detection path. The lasers are mounted orthogonal to one another so that one laser will provide a forward angle light scatter (FALS) signal in the detection path, and one laser will provide a side scatter signal in the detection path (i.e., the single detection optics are approximately in-line with the FALS laser and approximately orthogonal to the side scatter laser). The single detector path spectrally separates the forward and side scatter signals prior to applying them to their respective detectors for measurement.

9 Claims, 8 Drawing Sheets

(51) Int. Cl.
  *G01N 21/47* (2006.01)
  *G01N 15/00* (2006.01)
  *G01N 15/14* (2006.01)
  *G01N 15/10* (2006.01)

(52) U.S. Cl.
  CPC ........ *G01N21/645* (2013.01); *G01N 2015/008* (2013.01); *G01N 2015/1006* (2013.01); *G01N 2015/149* (2013.01); *G01N 2021/4711* (2013.01)

(56) References Cited

U.S. PATENT DOCUMENTS

| | | | |
|---|---|---|---|
| 5,260,764 A * | 11/1993 | Fukuda et al. | 356/73 |
| 5,436,717 A * | 7/1995 | Ogino | 356/72 |
| 5,521,699 A * | 5/1996 | Kosaka et al. | 356/73 |
| 5,548,395 A * | 8/1996 | Kosaka | 356/73 |
| 5,824,269 A * | 10/1998 | Kosaka et al. | 422/73 |
| 5,895,922 A | 4/1999 | Ho | |
| 6,054,712 A | 4/2000 | Komardin et al. | |
| 6,403,947 B1 | 6/2002 | Hoyt et al. | |
| 6,967,795 B2 * | 11/2005 | Cheng et al. | 359/891 |
| 6,979,570 B2 * | 12/2005 | Narisada | 436/63 |
| 7,477,363 B2 * | 1/2009 | Nagai | 356/73 |
| 7,843,561 B2 | 11/2010 | Rich | |
| 2008/0213915 A1 | 9/2008 | Durack et al. | |
| 2008/0304062 A1 * | 12/2008 | Kanda | 356/337 |
| 2011/0044695 A1 * | 2/2011 | Jun et al. | 398/130 |

OTHER PUBLICATIONS

Patent Application No. 201380000169.0, Chinese Patent Office, Office Action, dated Jul. 31, 2014.
Patent Application No. 201380000169.0, Chinese Patent Office, English Translation of Office Action, dated Jul. 31, 2014.

* cited by examiner

SYSTEM AND METHOD FOR MEASURING NARROW AND WIDE ANGLE LIGHT SCATTER ON A HIGH-SPEED CELL SORTING DEVICE

CROSS-REFERENCE TO RELATED APPLICATIONS

This application claims the benefit of U.S. Provisional Patent Application No. 61/583,074, filed Jan. 4, 2012, the text and drawings of which are hereby incorporated by reference in their entireties.

TECHNICAL FIELD OF THE DISCLOSURE

Background of the Disclosure

Flow cytometers and droplet based cell sorters are used in a variety of disciplines to perform optical measurements of individual particles as they flow through a single or multiple interrogation points. These optical measurements generally fall into two categories, namely scatter and fluorescence. Light scattering is a complex phenomenon that occurs when a particle interacts with a light beam and photons travel out of the incident beam. A single particle will scatter light from an incident beam over a wide range of angles. Scattered light is measured at the same wavelength as the incident light, unlike fluorescence where the measured light is of a longer wavelength than the wavelength of the incident beam. A flow cytometer or cell sorter will typically measure forward angle light scatter and wide angle light scatter.

Forward angle light scatter (FALS) is measured at small angles, typically less than about 15 degrees, from the propagation axis of the incident light beam. FALS is largely described by Mie scattering theory, and is a result of scattering by relatively large particles. The FALS measurement signal is proportional to the size of the particle, although it is not a true measure of particle size because the refractive index of the particle also affects the FALS signal intensity; however, in flow cytometry, FALS is commonly used as a rough estimator of particle size.

Wide angle light scatter is measured at relatively large angles from the propagation axis of the incident beam. Typically, a flow cytometer will measure either side scatter, where the detector is positioned to collect light that is scattered orthogonally to the incident beam, or back scatter, where the scattered light is measured nearly anti-parallel to the propagation axis of the incident beam. Wide angle light scatter is largely described by Rayleigh scattering theory, and is a result of scattering by relatively small particles. In flow cytometry, wide angle light scattering is used as a measure of granularity of the measured particle.

FALS and wide angle light scatter measurements provide different information about the morphology and physical properties of the particle, and are often used to discriminate between different types of particles. A common example of this is their use when analyzing blood cells, where lymphocytes, monocytes and granulocytes can be distinguished based upon the FALS and wide angle light scatter signals.

In droplet based cell sorters, it is common to perform all optical measurements of particles in a jet of fluid that has exited a nozzle. When the jet exits the nozzle, droplets will begin to form, which causes undulations in the stream which will refract and reflect the incident light and distort scatter measurements made more than a few hundred microns from the exit orifice of the nozzle. Advanced flow cytometers and cell sorters typically use multiple spatially separated laser interrogation points to perform fluorescence measurements. Traditionally, flow cytometers use a single laser (which is also one of the lasers used for fluorescence measurements) and two separate optical detection paths to measure FALS and wide angle light scatter. As the particle falls through the single laser beam, it scatters light at both narrow and wide angles. The system places separate collection optics at different positions in order to collect and analyze the light scattered at different angles.

It will be appreciated that the requirement for separate optical detection paths make the total optical measurement system more complicated. Accordingly, there is a need for improvements in the measurement of narrow and wide angle light scatter in high speed sorting devices. The presently disclosed embodiments are directed toward meeting this need.

SUMMARY OF THE DISCLOSED EMBODIMENTS

The various embodiments disclosed herein utilize multiple lasers that have different wavelengths and a single detection path. The lasers are mounted orthogonal to one another so that one laser will provide a FALS signal in the detection path, and one laser will provide a side scatter signal in the detection path (i.e., the single detection optics are approximately in-line with the FALS laser and approximately orthogonal to the side scatter laser). The single detector path spectrally separates the forward and side scatter signals prior to applying them to their respective detectors for measurement. The scatter lasers intersect on the sample jet sufficiently close to the nozzle so that undulations have not yet formed, thus reducing distortion. In some embodiments, the intersection of the two lasers occurs in the focal plane of the fluorescence collection optics of the flow cytometer with multiple laser interrogation points. Hence, additional collection optics for the scatter measurements are not needed.

In one embodiment, a system for measuring light scatter of a particle moving on a jetting axis is disclosed, the system comprising: a forward angle light scatter light source for emission of electromagnetic radiation of a first wavelength directed on a forward source axis; a side scatter light source for emission of electromagnetic radiation of a second wavelength directed on a side source axis; wherein the first wavelength is different than the second wavelength; wherein the forward source axis is substantially orthogonal to the side source axis; wherein the jetting axis, the forward source axis and the side source axis intersect at a focus spot; wherein when the particle is in the focus spot it will produce forward angle light scatter having the first wavelength and side scatter light having the second wavelength; a collection optic having an optic axis; wherein the optic axis and the forward source axis are selected from the group consisting of: parallel and collinear, such that the collection optic receives both forward angle light scatter and side scatter light; and a detector adapted to receive the combined forward angle light scatter and side scatter light received by the collection optic, the detector being operative to determine a forward angle light scatter component and a side scatter light component of the combined forward angle light scatter and side scatter light.

In another embodiment, a system for measuring light scatter of a particle moving on a jetting axis is disclosed, the system comprising: a forward angle light scatter light source for emission of electromagnetic radiation of a first wavelength; a side scatter light source for emission of electromagnetic radiation of a second wavelength; wherein the first wavelength is different than the second wavelength; wherein the electromagnetic radiation of a first wavelength and the electromagnetic radiation of a second wavelength meet at a focus spot; wherein when the particle is in the focus spot it will produce forward angle light scatter having the first wavelength and side scatter light having the second wavelength; a collection optic operative to receive both forward angle light scatter and side scatter light; and a detector adapted to receive the combined forward angle light scatter and side scatter light received by the collection optic, the detector being operative to determine a forward angle light scatter component and a side scatter light component of the combined forward angle light scatter and side scatter light.

In another embodiment, a scatter angle selection filter for angular selection of light scatter from a particle moving on a jetting axis is disclosed, comprising: a first optical filter operative to substantially transmit a first wavelength and substantially block a second wavelength, the first optical filter having a first side and a second side; wherein the first wavelength is different than the second wavelength; a second optical filter operative to substantially transmit the second wavelength and substantially block the first wavelength, the second optical filter having a third side and a fourth side; wherein the third side of the second optical filter abuts the first side of the first optical filter; and a third optical filter operative to substantially transmit the second wavelength and substantially block the first wavelength, the third optical filter having a fifth side and a sixth side; wherein the fifth side of the second optical filter abuts the second side of the first optical filter.

In another embodiment, a system for measuring light scatter of a particle moving on a jetting axis is disclosed, the system comprising: a scatter light source for emission of electromagnetic radiation of a first wavelength focused at a first spot; a fluorescence light source for emission of electromagnetic radiation of a second wavelength focused at a second spot; wherein first spot and the second spot intersect the jetting axis; a scatter detector operative to detect light from the scatter light source that is scattered by the particle; and a fluorescence detector operative to detect fluorescence from the particle that is caused by light from the fluorescence light source.

Other embodiments are also disclosed.

DETAILED DESCRIPTION OF THE DISCLOSED EMBODIMENTS

Figure 1:
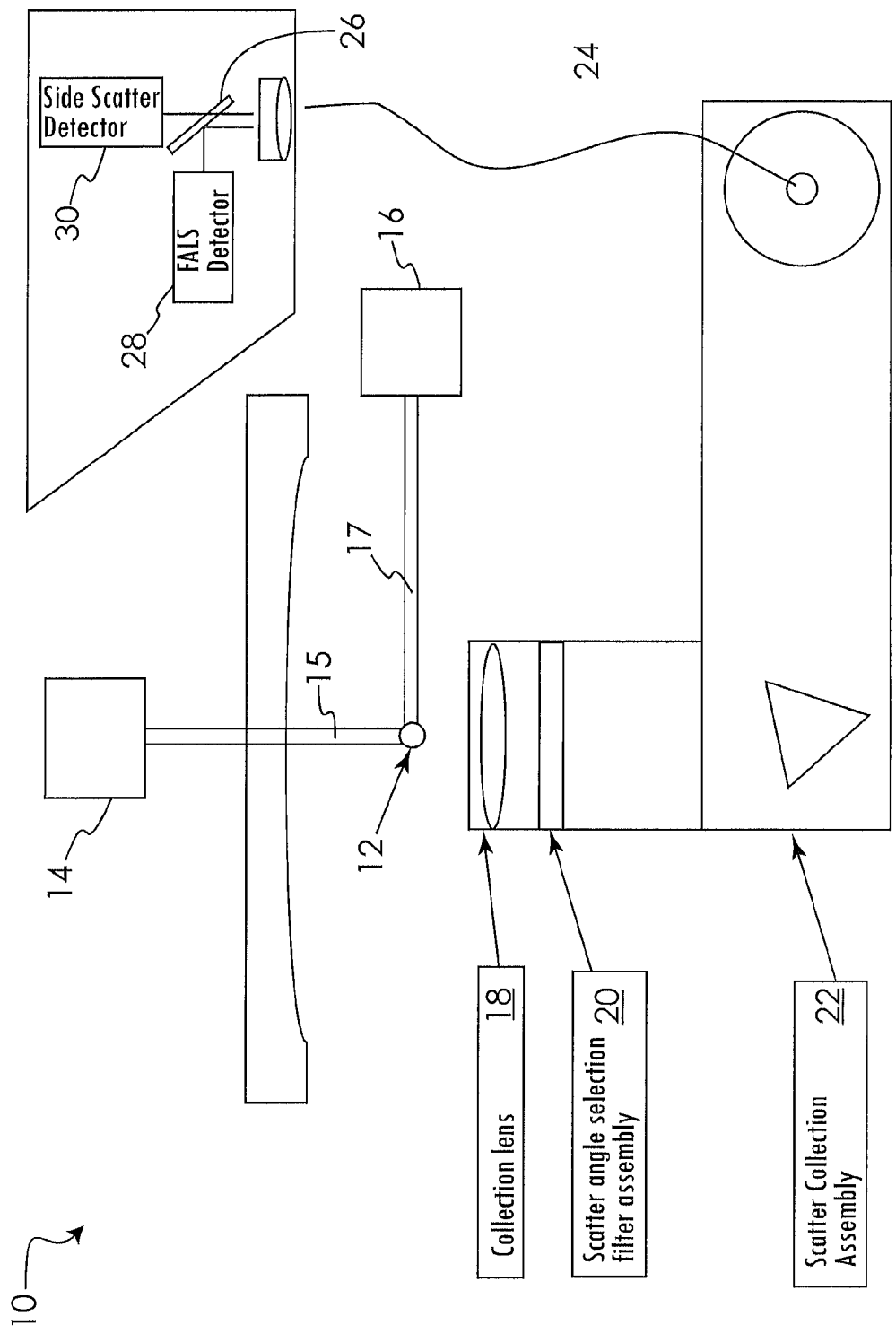
FIG. 1 is a schematic block diagram of a system for measuring narrow and wide angle light scatter according to one embodiment.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

The novel multiple laser scatter detection system disclosed herein uses two different lasers that have different emission wavelengths and a single scatter collection path for both FALS and wide angle scatter measurements. The lasers are mounted so that the beams are substantially orthogonal to one another. The single collection optic is then able to collect scattered light from both lasers. The specific angles measured by the FALS detection system are often important, so in some embodiments an angle selective optical filter assembly controls the detection angles of the FALS and side scatter collection. The collection optic focuses the scattered light onto an optical fiber, which delivers the scattered light to detection optics. The FALS and side scatter signals have different wavelengths, so optical filters and dichroic filters are used to separate the two signals into two different detectors, one for FALS and one for side scatter. In other embodiments, the light collected by the collection optic is digitized by an analog-to-digital converter and a data processor, such as a microprocessor executing software to calculate Fourier transforms, are used to differentiate between the two signals.

As shown in FIG. 1, a schematic diagram of one embodiment of the multiple laser scatter detection system is illustrated and indicated generally at 10. A jetting stream 12 of particles flows on a jetting axis orthogonal to the plane of the page. A FALS laser diode 14 and a side scatter laser diode 16 are positioned orthogonal to one another, so that they intersect on the stream 12. The sources 14, 16 may be any source of electromagnetic radiation, including but not limited to infrared light, visible light, ultraviolet light, x-rays, and other frequencies of electromagnetic radiation. The embodiments disclosed herein refer to laser diodes because they are commonly used in systems of this type, but no limitation on the scope of the claimed invention should be inferred thereby. The FALS laser diode 14 emits light on a forward source axis 15, while the side scatter laser diode 16 emits light on a side source axis 17 that is substantially orthogonal to the forward source axis 15. The emission wavelength of the FALS laser diode 14 is selected to be different than the emission wavelength of the side scatter laser diode 16. The lasers 14, 16 are both focused to a focus spots that intersect with one another and with the jetting axis, such that a particle on the jetting axis will move through the combined focus spot.

Light from lasers 14 and 16 scattered by a particle in the jetting stream 12 passes through a collection lens 18 and scatter angle selection filter assembly 20 before passing to a scatter collection assembly 22. This detection optic path is positioned so that the single detection optic may collect FALS from laser 14 (since the optical axes of both the laser 14 and the detection optics are substantially collinear or parallel) and also side scatter from the other laser 16 (since the optical axes of the laser 16 and the detection optics are substantially orthogonal). A fiber optic cable 24 carries the scattered light to a long-pass dichroic filter 26, where the two wavelengths are separated for detection by a FALS detector 28 and a side scatter detector 30. It will be appreciated that the system shown in FIG. 1 is but one embodiment, and that those skilled in the art will recognize from the present disclosure that the various optical and detection components may be arranged in various configurations in order to implement the concepts disclosed herein.

It will be appreciated from the above that one benefit of the presently disclosed embodiments is the use of separate illumination sources for scatter and fluorescence measurements. The selection of laser spot sizes and shapes in flow cytometry is a trade off between light intensity at the spot (favors smaller spot to get a higher intensity), and uniformity of illumination across the sample core (favors wider spot to get a larger illumination area). Light scatter is a much more intense signal (>2 or 3 orders of magnitude) than fluorescence. Using dedicated lasers for scatter and fluorescence allows for the use of optimized beam spot shapes, with larger aspect ratios for the scatter laser spots for improved stability, and smaller aspect ratios for fluorescence laser spots to allow for more intense illumination which will lead to greater sensitivity. Additionally, since scatter is used as a trigger signal in the vast majority of applications, a wider illumination spot size will result in fewer missed events (cells, beads, etc.) that could affect the performance (purity) of a sort if they arrived in the same droplet interval as a desired sort event.

In one embodiment described below, the FALS and wide angle scattering detection apparatus may be integrated into a Synergy™ flow cytometer available from iCyt Mission Technology, Inc., 2100 South Oak Street, Champaign, Ill. 61820, USA. In this embodiment, the scattering detection apparatus consists of four specific subassemblies: 1) A Forward Scatter Laser Assembly that comprises a fiber coupled laser and associated beam shaping optics mounted on the overall instrument Laser Delivery Assembly so as to illuminate the sample stream in a direction parallel to the stream illumination direction for the other fluorescence excitation lasers; 2) A Side Scatter Laser Assembly that comprises a fiber coupled laser with associated beam shaping optics mounted so as to illuminate the sample stream in a direction substantially orthogonal to the forward scatter laser; 3) Light Collection Optics Assembly to collect and condition light scattered from the sample from both Forward and Side Scatter lasers and transfer this light to the detectors; and 4) Detection Optics and photomultiplier tubes (PMTs) to separate out the signals and report the light levels in each scattering direction to the processing system.

Forward Scatter Laser Assembly

An 808 nm laser is coupled into a single mode polarization maintaining fiber. The laser is attached to the Laser Delivery Assembly (LDA) of the Synergy™ flow cytometer. Beam shaping optics collimate the output from the fiber and produce an approximately 20 micron high by 200 micron wide beam spot that is optimized for forward scatter measurement and is focused at the sample stream. The spot is focused at the highest spot as defined by the 5-spot Reflection® Collection Optics (RCO5) used in the Synergy™ cytometer. Polarization of the light is set to be vertical at the sample stream to optimize the scattered light signal.

Side Scatter Laser Assembly

Figure 2:
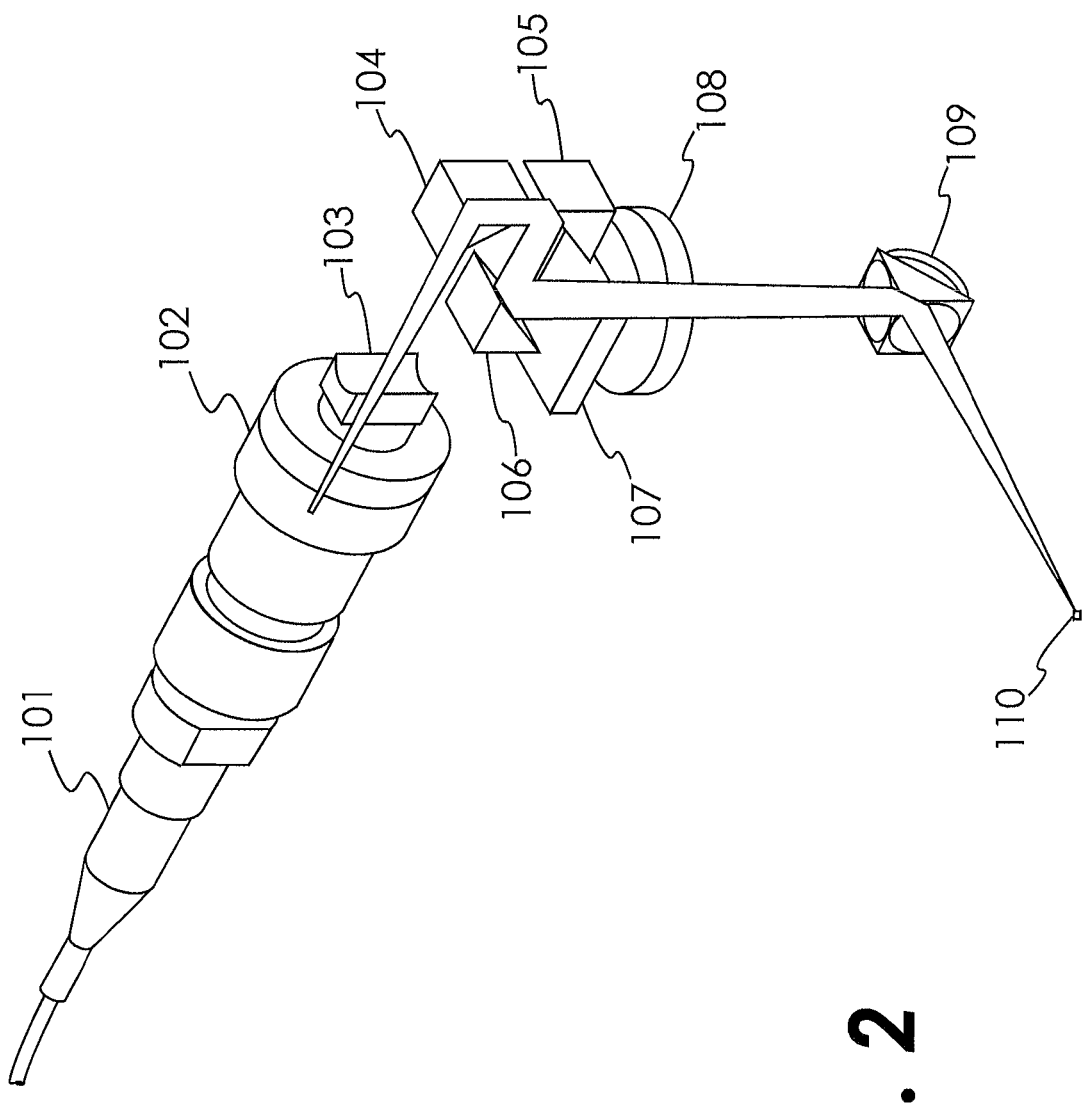
FIG. 2 is a perspective schematic view of a side scatter laser assembly according to one embodiment.

As shown in FIG. 2, an 830 nm laser coupled into a single mode polarization maintaining optical fiber 101 is mounted on the LDA of the Synergy™ flow cytometer. The optical fiber 101 transfers the laser light from the laser to the Side Scatter (SSC) Laser Assembly of FIG. 2 that is mounted in the sorting module of the Synergy™ instrument. Beam shaping optics in the assembly include a fiber collimator 102, concave cylindrical lens 103, beam folding prisms 104-106, convex cylindrical lens 107, and convex spherical lens 108 to produce an approximately 20 micron high by 200 micron wide spot 110 at the sample stream coincident with the Forward Scatter Laser focus spot, and incident on the stream in a direction that is normal to the forward scatter illumination direction. Polarization of the light is set to be vertical at the sample stream to optimize the scattered light signal. The folded beam path allows for a compact assembly.

Light Collection Optics Assembly

Figure 3:
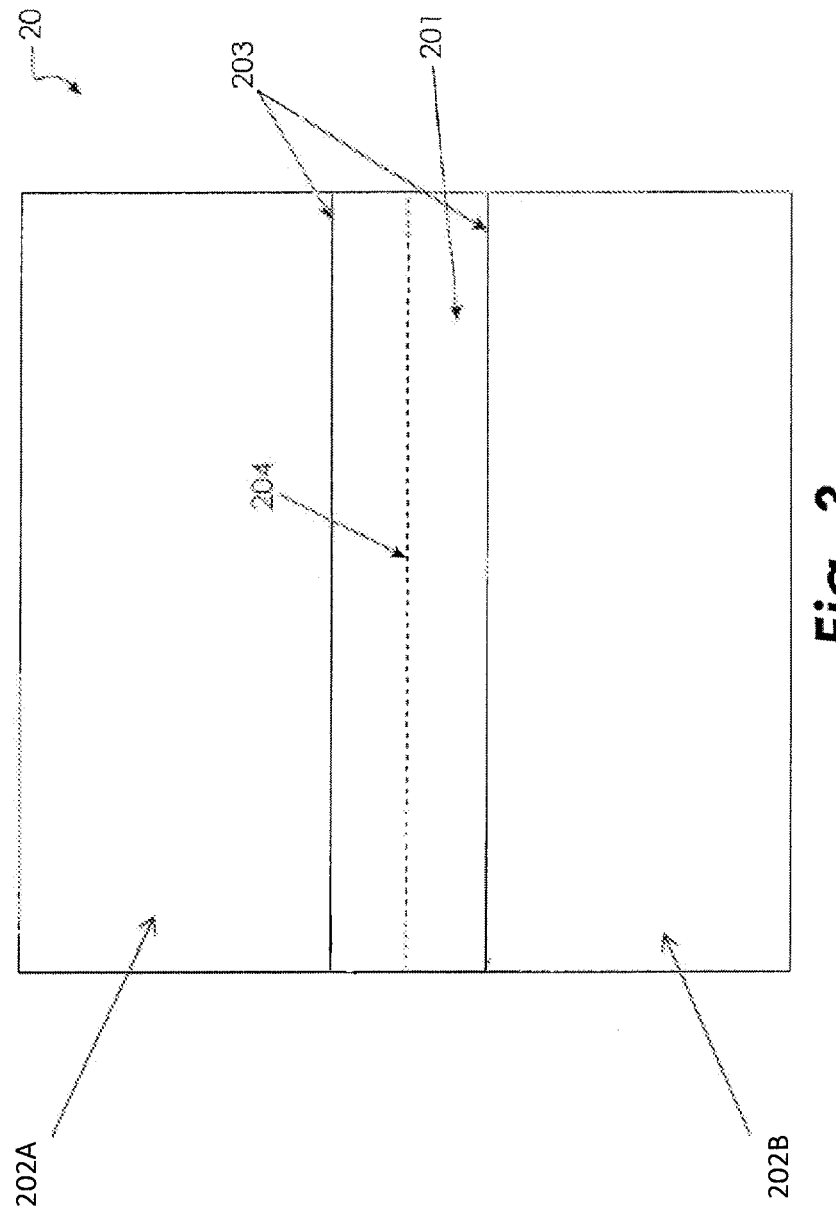
FIG. 3 is a schematic cross-sectional diagram of a scatter angle selection filter assembly according to one embodiment.

Referring once again to FIG. 1, the single Light Collection Optics Assembly is positioned to collect light scattered from the sample stream in a direction that is both collinear or parallel to the forward scatter incident light (from laser 14) and perpendicular to the side scatter incident light (from laser 16). A 0.5 NA collection lens 18 collects light scattered from the sample at angles up to :30 degrees. Light incident between :4 degrees is blocked by a beam blocker (not shown) in front of the lens 18 to prevent unscattered light from entering the detection system. Wavelength selective filters further condition the scattered signal. The first filter blocks all wavelengths less than the 2 scattering laser wave lengths. As shown in FIG. 3, a novel scatter angle selection filter assembly 20 blocks all side-scattered light incident at an angle less than ±7 degrees while also blocking all forward scattered light incident at angles greater than ±7 degrees and less than ±4 degrees. The scatter angle selection filter assembly 20 comprises an optical filter 201 that transmits the forward scatter (FSC) laser 14 wavelength and blocks the side scatter (SSC) laser 16 wavelength, and optical filters 202A and 202B that transmit the SSC laser 16 wavelength and block the FSC laser 14 wavelength, such that the edges 203 of the filter 201 define the high semi-angle of FSC that is collected by the system. The optical axis (0 degrees) of the detector system is indicated at 204. A separate lens system (not shown) then focuses all the light into an optical fiber 24 for detection in the detector module.

Detection Optics and Photomultiplier Tube (PMT) Assembly

Figure 4:
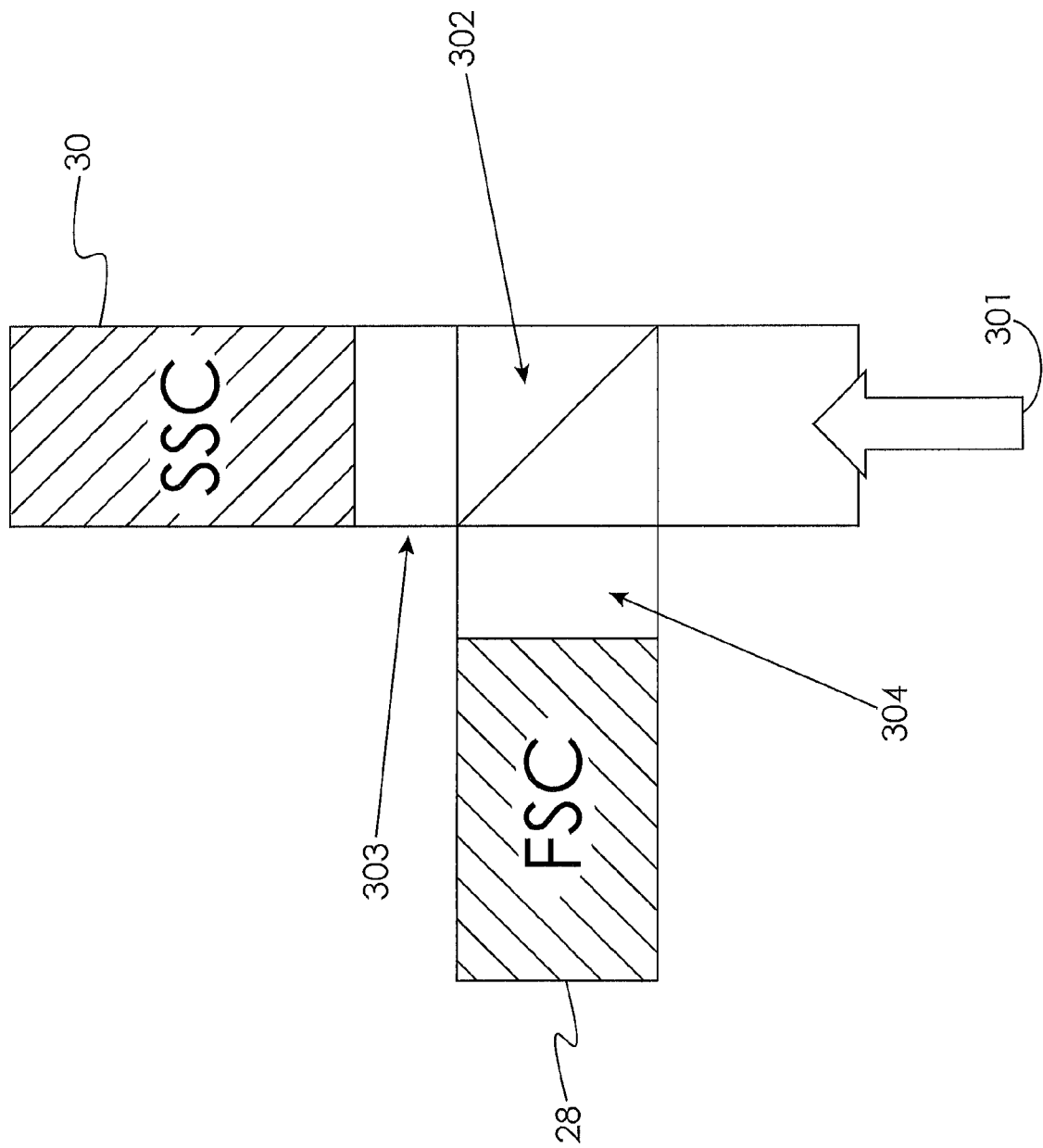
FIG. 4 is a schematic diagram of a detection optics and photomultiplier tube assembly according to one embodiment.

With reference to FIGS. 1 and 4, the forward and side scatter signals are separated and detected by the Detection Optics and Photo Multiplier Tube (PMT) assembly by separating out the wavelengths with optical filters. The combined scattered light from the Light Collection and Conditioning Assembly is input at 301 from the fiber optic 24. A long-pass dichroic filter 302, is such as a model t808rb available from Chroma Technology Corporation, 10 Imtec Lane, Bellows Falls, Vt. 05101, transmits the SSC laser 16 wavelength light to the SSC detector 30 while blocking the FSC laser 14 wavelength light from reaching the SSC detector 30, and also reflects the FSC laser 14 wavelength light to the FSC detector 28 and blocks the SSC laser 16 wavelength light from reaching the FSC detector 28. Light enters the SSC detector 30 though a long-pass edge filter 303 (such as a Chroma E825LP; or a model LP02-808RS available from Semrock, Inc., 3625 Buffalo Road, Suite 6, Rochester, N.Y. 14624). Light enters the FSC detector 28 through a single-band bandpass filter 304, such as a Chroma ET792/50 or Semrock FF01-785/62. This combination of filters allows each detector 28,30 to only receive the scattered light (forward or side) that the detector is supposed to measure. Because the FSC laser 14 and the SSC laser 16 are chosen to have different emission wavelengths, both the forward and side scattered light may be collected with a single collection optic, and then the contributions from each laser may later be separated for individual measurement. As discussed above, such separation may be accomplished in other embodiments using digital techniques, such a Fourier transforms, which allow the individual frequency components to be separated and measured from the combined signal.

EXAMPLES

The multiple laser/single collection optic scatter detection system described above was installed onto an iCyt® Synergy™ cell sorter and fully aligned. The system was then used to measure the FALS and side scatter of a large variety of samples. FIGS. 5-8 display the results of these experiments, which are summarized below.

Blood Scatter Measurements

Figure 5:
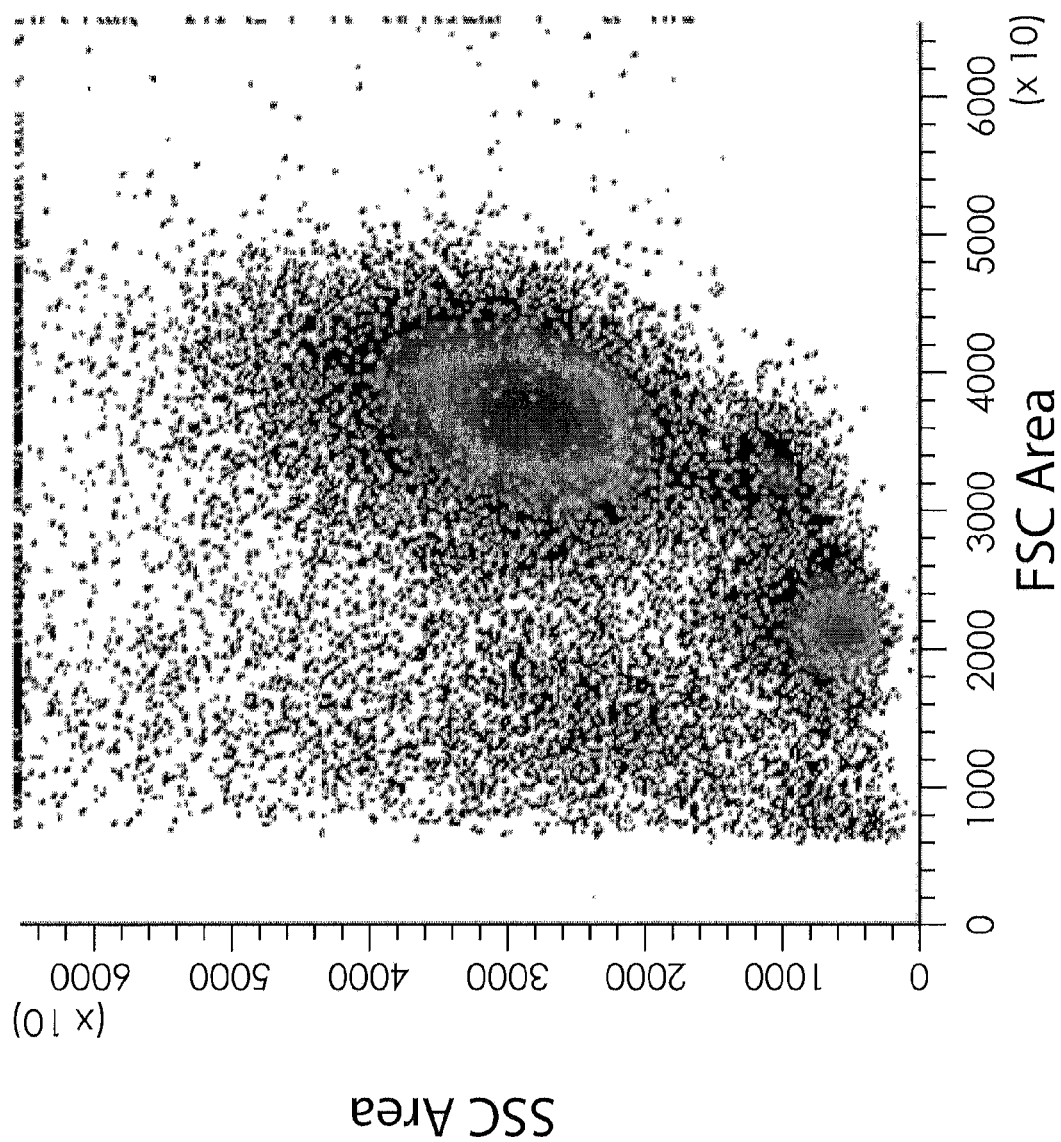
FIG. 5 is a plot of side scatter area vs. forward scatter area measurements of blood samples made using one embodiment system, showing that the lymphocyte, monocyte and granulocyte populations are clearly distinguishable.

An analysis of blood samples was made using the multiple laser scatter detection system disclosed above. The samples were donated human blood collected in an EDTA Vacutainer Collection tube (available from Becton, Dickinson and Company, 1 Becton Drive, Franklin Lakes, N.J. 07417-1880, USA), and prepped using iCyt® RBC Lysis Buffer (available from iCyt Mission Technology, Inc., 2100 South Oak Street, Champaign, Ill. 61820, USA) to remove red blood cells. FIG. 5 shows a plot of side scatter area vs. forward scatter area measurements using the multiple laser scatter detection system disclosed above. This data shows that the lymphocyte, monocyte and granulocyte populations are clearly distinguishable by virtue of their different forward and side scatter properties.

Polystyrene Microparticle Measurements

Figure 6:
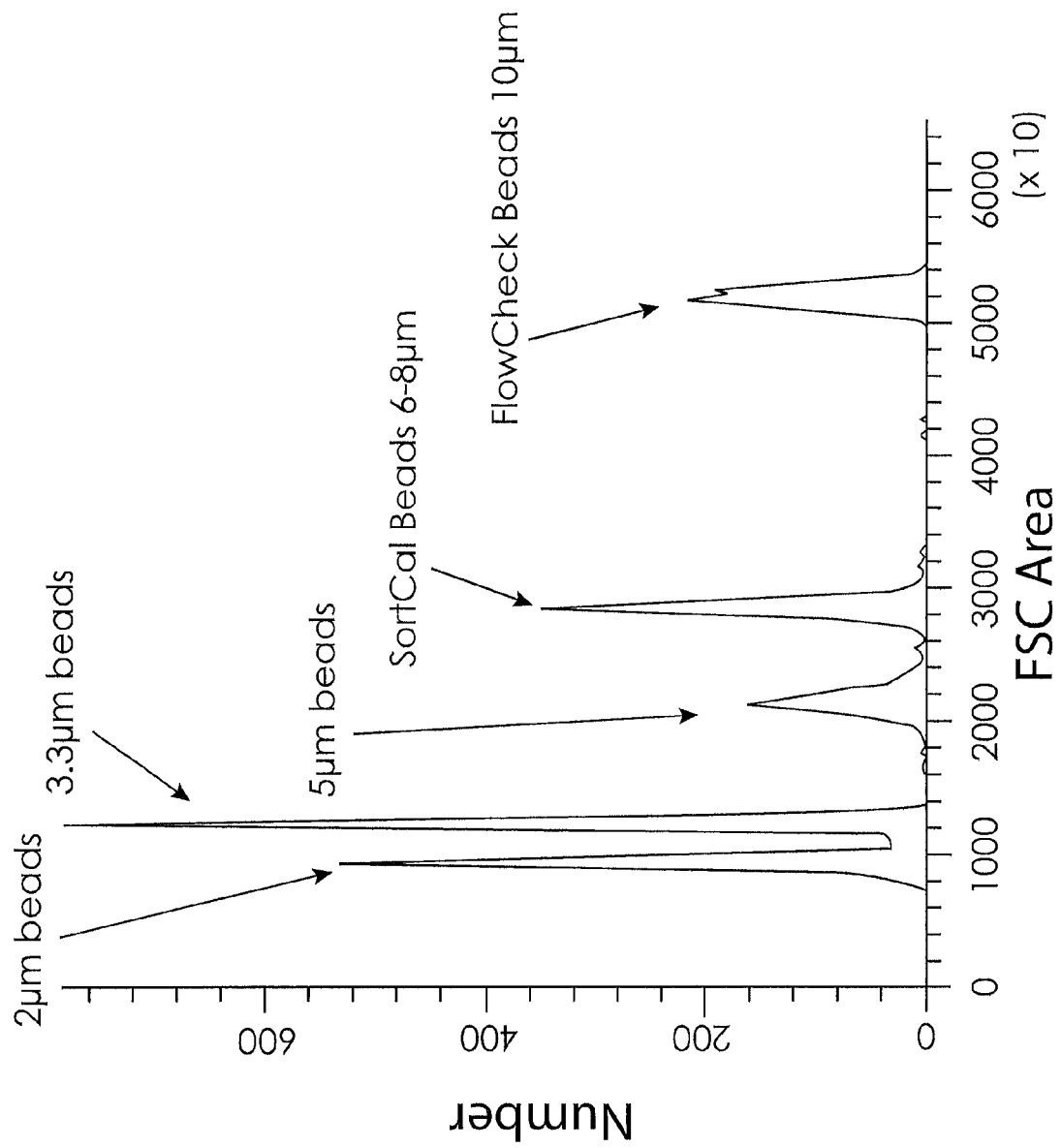
FIG. 6 is a plot of the forward scatter area measurements of polystyrene microparticles made using one embodiment system, showing that the FALS measurement can be used to identify individual populations of polystyrene microparticles in a mixture based on the size of the microparticle.

Mixtures of polystyrene microparticles, or beads, were measured using the multiple laser scatter detection system disclosed above. FIG. 6 plots only the forward scatter area data. This data shows that the FALS measurement can be used to identify individual populations of polystyrene microparticles in a mixture based on the size of the microparticle.

Figure 7:
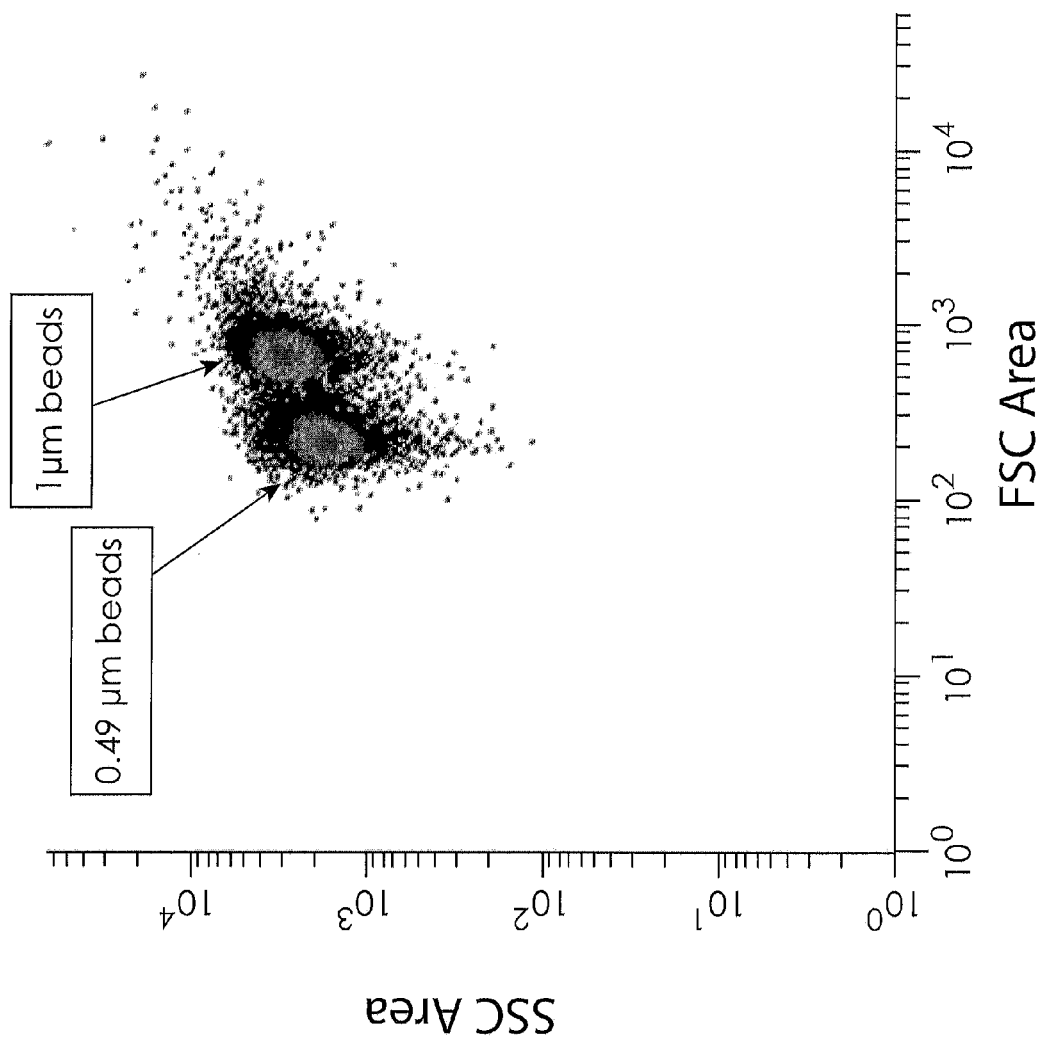
FIG. 7 is a plot of the side scatter area vs. the forward scatter area when two different size polystyrene microparticles are measured using one embodiment system, showing that the 0.49 micron polystyrene beads and 1 micron polystyrene beads are clearly distinguishable.

FIG. 7 plots the side scatter area vs. the forward scatter area when two different size beads are measured in the cell sorter. This figure shows the scatter measurements of a mixture of 0.49 micron polystyrene beads and 1 micron polystyrene beads. This data shows that the multiple laser scatter detection system disclosed above has the ability to resolve small particles.

Bacteria Measurements

Figure 8:
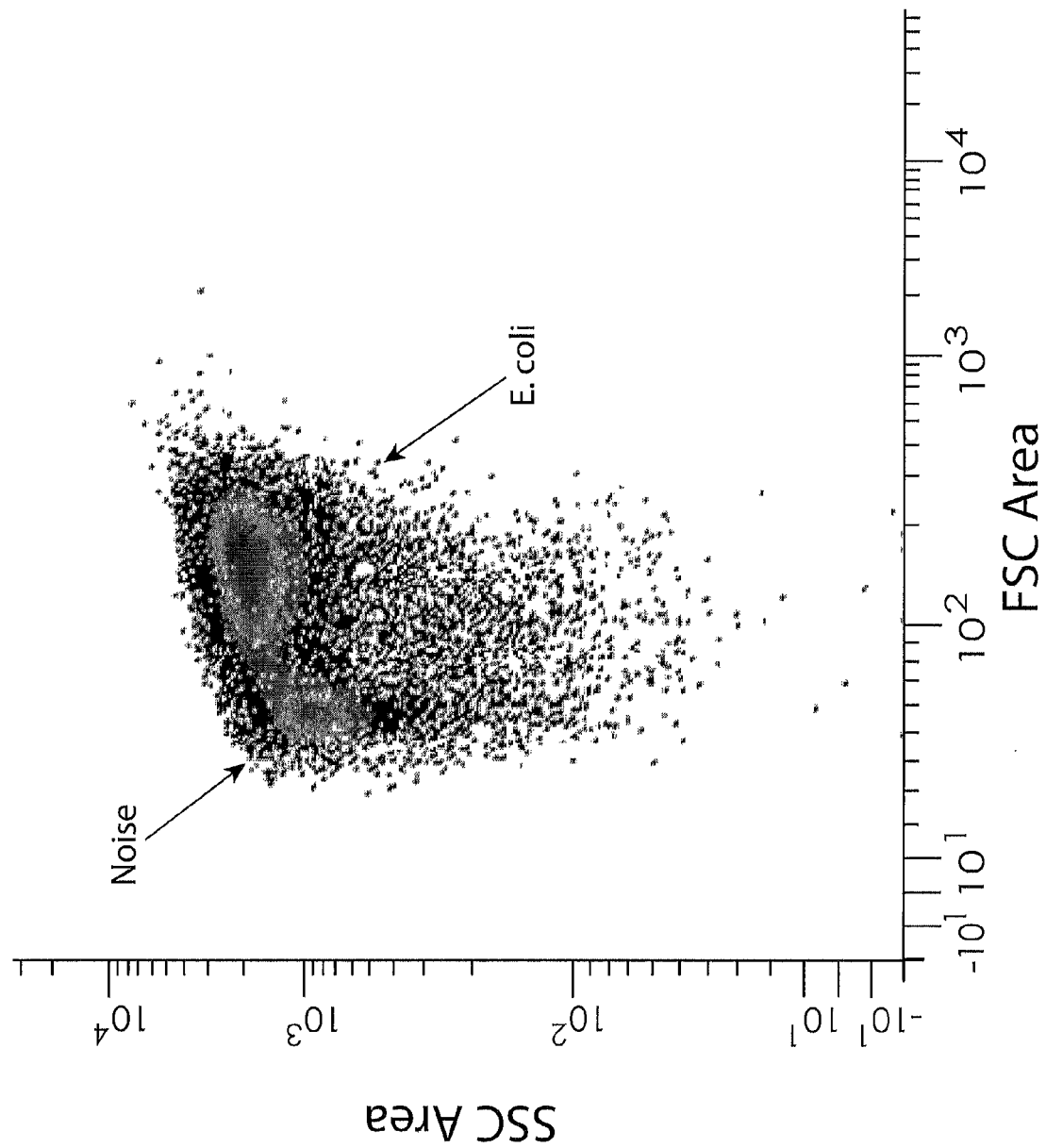
FIG. 8 plots side scatter area vs. forward scatter area when a sample of E. coli bacteria were measured using one embodiment system.

FIG. 8 plots side scatter area vs. forward scatter area when a sample of E. coli bacteria were measured the cell sorter. This figure shows that E. coli bacteria can be resolved from background noise based on scatter measurements from the multiple laser scatter system disclosed above.

CONCLUSION

It will be appreciated from the above description that a novel multiple laser light/single collection optic scatter measurement system has been described herein. The system uses separate lasers to excite forward angle light scatter and side scatter and includes a single detection optical path for both forms of scattered light. The dedicated scatter lasers have different emission wavelengths from one another so that their individual contributions may be segregated from the combined scattered light that is collected from the single collection optics. The dedicated scatter lasers have spot shapes that are optimized for stability and scatter detection, whereas traditional flow cytometers use the same laser for scatter and fluorescence measurement so that a tradeoff must be made between scatter performance and fluorescence sensitivity. Additionally, in the embodiments disclosed herein the intersection of the scatter lasers provides a physical landmark in three dimensions for the properly aligned nozzle position, and this landmark aids in the alignment of the optical system for a multiple laser cell sorter. The multiple laser scatter system has been used to perform scatter measurements on several samples successfully.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. It is also contemplated that structures and features embodied in the present examples can be altered, rearranged, substituted, deleted, duplicated, combined, or added to each other. The articles "the", "a" and "an" are not necessarily limited to mean only one, but rather are inclusive and open ended so as to include, optionally, multiple such elements.

What is claimed:

1. A system for measuring light scatter of a particle moving on a jetting axis, the system comprising:
    a forward angle light scatter light source for emission of electromagnetic radiation of a first wavelength directed on a forward source axis;
    a side scatter light source for emission of electromagnetic radiation of a second wavelength directed on a side source axis;
    wherein the first wavelength is different than the second wavelength;
    wherein the forward source axis is substantially orthogonal to the side source axis;
    wherein the jetting axis, the forward source axis and the side source axis intersect at a focus spot;
    wherein when the particle is in the focus spot it will produce forward angle light scatter having the first wavelength and side scatter light having the second wavelength;
    a collection optic having an optic axis;
    wherein the optic axis and the forward source axis are selected from the group consisting of: parallel and collinear, such that the collection optic receives both forward angle light scatter and side scatter light;
    a detector positioned in relation to the collection optic such that forward angle light scatter and side scatter light received by the collection optic impinge on the detector as combined forward angle light scatter and side scatter light, the detector producing a first output representative of a forward angle light scatter component of the combined forward angle light scatter and side scatter light, the detector producing a second output representative of a side scatter light component of the combined forward angle light scatter and side scatter light; and
    wherein the collection optic comprises a collection lens and a scatter angle selection filter assembly comprising:
        a first optical filter operative to substantially transmit the first wavelength and substantially block the second wavelength, the first optical filter having a first side, a second side, and a first optical filter axis;
        wherein the first optical filter axis is substantially collinear with the optic axis;
        a second optical filter operative to substantially transmit the second wavelength and substantially block the first wavelength, the second optical filter having a third side and a fourth side;

wherein the third side of the second optical filter abuts the first side of the first optical filter; and a third optical filter operative to substantially transmit the second wavelength and substantially block the first wavelength, the third optical filter having a fifth side and a sixth side;

wherein the fifth side of the second optical filter abuts the second side of the first optical filter.

2. The system of claim 1, wherein the forward angle light scatter light source comprises a first laser and the side scatter light source comprises a second laser.

3. The system of claim 1, wherein said electromagnetic radiation comprises visible light.

4. A system for measuring light scatter of a particle moving on a jetting axis, the system comprising:

a forward angle light scatter light source for emission of electromagnetic radiation of a first wavelength;

a side scatter light source for emission of electromagnetic radiation of a second wavelength;

wherein the first wavelength is different than the second wavelength;

wherein the electromagnetic radiation of a first wavelength and the electromagnetic radiation of a second wavelength meet at a focus spot;

wherein when the particle is in the focus spot it will produce forward angle light scatter having the first wavelength and side scatter light having the second wavelength;

a collection optic operative to receive both forward angle light scatter and side scatter light;

a detector positioned in relation to the collection optic such that forward angle light scatter and side scatter light received by the collection optic impinge on the detector as combined forward angle light scatter and side scatter light, the detector producing a first output representative of a forward angle light scatter component of the combined forward angle light scatter and side scatter light, the detector producing a second output representative of a side scatter light component of the combined forward angle light scatter and side scatter light; and wherein the collection optic comprises a collection lens and a scatter angle selection filter assembly comprising:

a first optical filter operative to substantially transmit the first wavelength and substantially block the second wavelength, the first optical filter having a first side, a second side, and a first optical filter axis;

wherein the first optical filter axis is substantially collinear with the optic axis;

a second optical filter operative to substantially transmit the second wavelength and substantially block the first wavelength, the second optical filter having a third side and a fourth side;

wherein the third side of the second optical filter abuts the first side of the first optical filter; and a third optical filter operative to substantially transmit the second wavelength and substantially block the first wavelength, the third optical filter having a fifth side and a sixth side;

wherein the fifth side of the second optical filter abuts the second side of the first optical filter.

5. The system of claim 4, wherein:

the electromagnetic energy of a first wavelength is directed on a forward source axis;

the electromagnetic energy of a second wavelength is directed on a side source axis;

the forward source axis is substantially orthogonal to the side source axis;

the jetting axis, the forward source axis and the side source axis intersect at the focus spot;

the collection optic has an optic axis; and the optic axis and the forward source axis are selected from the group consisting of: parallel and collinear.

6. The system of claim 4, wherein the forward angle light scatter light source comprises a first laser and the side scatter light source comprises a second laser.

7. The system of claim 4, wherein said electromagnetic radiation comprises visible light.

8. A scatter angle selection filter for angular selection of light scatter from a particle moving on a jetting axis, comprising:

a first optical filter operative to substantially transmit a first wavelength and substantially block a second wavelength, the first optical filter having a first side and a second side;

wherein the first wavelength is different than the second wavelength;

a second optical filter operative to substantially transmit the second wavelength and substantially block the first wavelength, the second optical filter having a third side and a fourth side;

wherein the third side of the second optical filter abuts the first side of the first optical filter; and a third optical filter operative to substantially transmit the second wavelength and substantially block the first wavelength, the third optical filter having a fifth side and a sixth side;

wherein the fifth side of the second optical filter abuts the second side of the first optical filter.

9. The scatter angle selection filter of claim 8, further comprising:

a forward angle light scatter light source for emission of electromagnetic radiation of the first wavelength directed on a forward source axis;

a side scatter light source for emission of electromagnetic radiation of the second wavelength directed on a side source axis;

wherein the forward source axis is substantially orthogonal to the side source axis;

wherein the jetting axis, the forward source axis and the side source axis intersect at a focus spot;

wherein when the particle is in the focus spot it will produce forward angle light scatter having the first wavelength and side scatter light having the second wavelength; and a collection optic having an optic axis;

wherein the first optical filter has a first optical filter axis;

wherein the first optical filter axis is substantially collinear with the optic axis; and wherein the optic axis and the forward source axis are selected from the group consisting of: parallel and collinear, such that the collection optic receives both forward angle light scatter and side scatter light.

* * * * *